US012782252B2

(12) United States Patent
Shiozawa

(10) Patent No.: US 12,782,252 B2
(45) Date of Patent: Nov. 3, 2026

(54) EVALUATION METHOD

(71) Applicant: SUMITOMO RUBBER INDUSTRIES, LTD., Kobe (JP)

(72) Inventor: Tomomi Shiozawa, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 312 days.

(21) Appl. No.: 18/106,044

(22) Filed: Feb. 6, 2023

(65) Prior Publication Data

US 2023/0280248 A1 Sep. 7, 2023

(30) Foreign Application Priority Data

Mar. 2, 2022 (JP) ................................ 2022-032075

(51) Int. Cl.

| | |
|---|---|
| ***G01N 3/06*** | (2006.01) |
| ***C08K 3/30*** | (2006.01) |
| ***C08K 3/36*** | (2006.01) |
| ***G01N 3/08*** | (2006.01) |
| ***G01N 15/08*** | (2006.01) |
| ***G01N 23/083*** | (2018.01) |
| ***G01N 23/201*** | (2018.01) |
| ***G01N 33/44*** | (2006.01) |

(52) U.S. Cl.

CPC ................ *G01N 3/06* (2013.01); *G01N 3/08* (2013.01); *G01N 15/088* (2013.01);

(Continued)

(58) Field of Classification Search

CPC .......... G01N 3/06; G01N 3/08; G01N 23/201; G01N 23/083; G01N 33/445;

(Continued)

(56) References Cited

U.S. PATENT DOCUMENTS

2007/0009094 A1 1/2007 Anno
2008/0002812 A1* 1/2008 Ito ........................ G01N 23/201 378/88
2020/0206572 A1 7/2020 Komatsu

FOREIGN PATENT DOCUMENTS

JP 2004-294120 A 10/2004
JP WO2006/004185 A1 1/2006

(Continued)

OTHER PUBLICATIONS

Rinnerthaler et al., "Scanning Small Angle X-ray Scattering Analysis of Human Bone Sections", Calcif Tissue Int (1999) 64: 422-429 , Aug. 12, 1997 <https://pubmed.ncbi.nlm.nih.gov/10203419/> (Year: 1999).*

(Continued)

*Primary Examiner* — Jonathan M Dunlap

(74) *Attorney, Agent, or Firm* — Birch, Stewart, Kolasch & Birch, LLP

(57) ABSTRACT

Provided is an evaluation method that can easily evaluate the percentage of voids in a rubber material. The present disclosure relates to an evaluation method including evaluating the percentage of voids in a rubber material with a strain applied thereto based on the $\varphi_{void}$ calculated from the following Equation (1) using the transmittance and thickness of the rubber material with no strain applied thereto and the transmittance and thickness of the rubber material with the strain applied thereto.

$$\phi_{void} = 1 - \rho_s/\rho_0 = 1 - \ln\left(\frac{I_s}{I_0}\right) \Big/ \ln\left(\frac{I}{I_0}\right) \times (t_0/t_s) \quad (1)$$

11 Claims, 1 Drawing Sheet

(52) U.S. Cl.
CPC ......... *G01N 23/201* (2013.01); *G01N 33/445* (2013.01); *C08K 3/30* (2013.01); *C08K 3/36* (2013.01); *G01N 2015/0846* (2013.01); *G01N 23/083* (2013.01); *G01N 2203/0641* (2013.01); *G01N 2223/649* (2013.01)

(58) Field of Classification Search
CPC ......... G01N 2203/0641; G01N 15/088; G01N 2015/0846; G01N 2223/649; C08K 3/30; C08K 3/36
See application file for complete search history.

(56) References Cited

FOREIGN PATENT DOCUMENTS

| | | |
|---|---|---|
| JP | 2009-128331 A | 6/2009 |
| JP | 2017-83182 A | 5/2017 |
| JP | 2020-103581 A | 7/2020 |

OTHER PUBLICATIONS

Zhang et al., "Nanocavitation around a crack tip in a soft nanocomposite: A scanning microbeam small angle X-ray scattering study" , Journal of Polymer Science Part B: Polymer Physics, vol. 53, Iss. 6, Mar. 2015 <https://doi.org/10.1002/polb.23651> (Year: 2015).*

Lorenz-Haas et al., "Scanning Microfocus Small-Angle X-ray Scattering: A New Tool to Investigate Defects at Polymer-Polymer Interfaces", Langmuir 2003, vol. 19, Iss. 7, pp. 3056-3061 <https://pubs.acs.org/doi/10.1021/la026693%2B> (Year: 2003).*

Zhang et al., "Nanocavitation in Carbon Black Filled Styrene-Butadiene Rubber under Tension Detected by Real Time Small Angle X-ray Scattering", Macromolecules, vol. 45, Jan. 27, 2012, pp. 1529-1543.

Zhang et al., "Opening and Closing of Nanocavities under Cyclic Loading in a Soft Nanocomposite Probed by Real-Time Small-Angle X-ray Scattering" Macromolecules, vol. 46, Jan. 24, 2013, pp. 900-913.

* cited by examiner

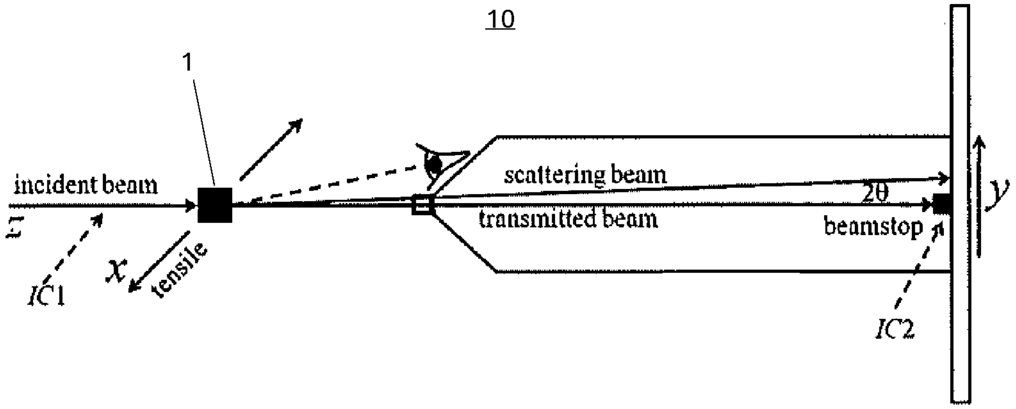
10
1
incident beam
scattering beam
2θ
transmitted beam
beamstop
tensile
x
y
IC1
IC2

EVALUATION METHOD

TECHNICAL FIELD

The present disclosure relates to a method of evaluating a rubber material.

BACKGROUND ART

It is known that small voids (cavities) may be formed in a rubber material when strain is applied thereto (see, for example, Non-Patent Literatures 1 and 2).

NON PATENT LITERATURE

Citation List

Non-Patent Literature 1: Macromolecules 2012, 45, 1529-1543

Non-Patent Literature 2: Macromolecules 2013, 46, 900-913

SUMMARY OF DISCLOSURE

Technical Problem

In Non-Patent Literatures 1 and 2, the change in scattering intensity of a rubber material that occurs with void formation is measured by small-angle X-ray scattering analysis (SAXS analysis) to quantitatively evaluate voids. Such methods require measurements over a wide region of wavenumbers. In practice, however, since the area of the view plane of the detector is limited, the wavenumber region to be measured is limited. Thus, there is still room for improvement in that voids within some region cannot be observed.

The present disclosure aims to solve the aforementioned problem and provide an evaluation method that can easily evaluate the percentage of voids in a rubber material.

Solution to Problem

The present disclosure relates to an evaluation method, including evaluating a percentage of voids in a rubber material with a strain applied thereto based on a $\varphi_{void}$ calculated from the following Equation (1) using a transmittance and thickness of the rubber material with no strain applied thereto and a transmittance and thickness of the rubber material with the strain applied thereto, $$\phi_{void} = 1 - p_s/p_0 = 1 - \ln\left(\frac{I_s}{I_0}\right)\Big/\ln\left(\frac{I}{I_0}\right)\times(t_0/t_s) \quad (1)$$

wherein

- $\rho_0$: a density of the rubber material with no strain applied thereto,
- $\rho_s$: a density of the rubber material with the strain applied thereto,
- $I/I_0$: the transmittance of the rubber material with no strain applied thereto,
- $I_s/I_0$: the transmittance of the rubber material with the strain applied thereto,
- $I_0$: an intensity of a beam incident on the rubber material,
- I: an intensity of the beam transmitted through the rubber material with no strain applied thereto,
- $I_s$: an intensity of the beam transmitted through the rubber material with the strain applied thereto,

- $t_0$: the thickness of the rubber material with no strain applied thereto, and
- $t_s$: the thickness of the rubber material with the strain applied thereto.

Advantageous Effects of Disclosure

According to the present disclosure, the percentage of voids in a rubber material with a strain applied thereto can be easily evaluated based on the $\varphi_{void}$ calculated from Equation (1) using the transmittance and thickness of the rubber material with no strain applied thereto and the transmittance and thickness of the rubber material with the strain applied thereto.

BRIEF DESCRIPTION OF THE DRAWINGS

The FIGURE shows an X-ray detector according to an embodiment.

DESCRIPTION OF EMBODIMENTS

The present disclosure relates to an evaluation method including evaluating the percentage of voids in a rubber material with a strain applied thereto based on the $\varphi_{void}$ calculated from the following Equation (1) using the transmittance and thickness of the rubber material with no strain applied thereto and the transmittance and thickness of the rubber material with the strain applied thereto, $$\phi_{void} = 1 - p_s/p_0 = 1 - \ln\left(\frac{I_s}{I_0}\right)\Big/\ln\left(\frac{I}{I_0}\right)\times(t_0/t_s) \quad (1)$$

wherein

- $\rho_0$: the density of the rubber material with no strain applied thereto,
- $\rho_s$: the density of the rubber material with the strain applied thereto,
- $I/I_0$: the transmittance of the rubber material with no strain applied thereto,
- $I_s/I_0$: the transmittance of the rubber material with the strain applied thereto,
- $I_0$: the intensity of the beam incident on the rubber material,
- I: the intensity of the beam transmitted through the rubber material with no strain applied thereto,
- $I_s$: the intensity of the beam transmitted through the rubber material with the strain applied thereto,
- $t_0$: the thickness of the rubber material with no strain applied thereto, and
- $t_s$: the thickness of the rubber material with the strain applied thereto.

When voids are formed in a rubber material, the rubber material usually has an increased volume while maintaining the mass, resulting in a lower density ($\rho_s<\rho_0$). Thus, a rubber material having a higher percentage of voids has a larger $\varphi_{void}$ calculated by "$1-\rho_s/\rho_0$". This relationship may be used to evaluate (quantitatively evaluate) the percentage of voids from $\varphi_{void}$. Moreover, since $\varphi_{void}$ can be calculated only from the transmittance and thickness of the rubber material, the percentage of voids can be evaluated easily. Furthermore, since according to the present disclosure, the voids present in the volume irradiated with X-rays are evaluable, the voids in the entire rubber material can be evaluated by irradiating the entire rubber material with X-rays.

Here, the transmittance ($I/I_0$) of the material is generally determined by the formulation of the material and represented by Equation (2) below. Thus, "$1-\rho_s/\rho_0$" may be transformed into an equation consisting of transmittance and thickness using Equation (2):

$$\frac{I}{I_0} = \exp(-\mu t) = \exp(-\mu_m \rho t) \quad (2)$$

wherein

I: the intensity of the beam incident on the material, $I_0$: the intensity of the beam transmitted through the material, μ: the linear absorption coefficient, $\mu_m$: the mass absorption coefficient, ρ: the density of the material, and t: the thickness of the material.

The thickness ($t_s$) of the rubber material with the strain applied thereto in Equation (1) may be determined by measuring the actual thickness, or may be calculated from the following Equation (3):

$$t_s = t_0/\sqrt{\epsilon/100} \quad (3)$$

wherein $t_0$: the thickness of the rubber material with no strain applied thereto, $t_s$: the thickness of the rubber material with the strain applied thereto, and ε: the amount (%) of strain.

Assuming that the rubber material deforms at a Poisson's ratio of 0.5, since the volume does not change, the rubber material can be regarded to deform at the same rate in the direction orthogonal to the strain. Thus, the thickness ($t_s$) of the rubber material with the strain applied thereto can be calculated from Equation (3). The use of Equation (3) makes it possible to more easily evaluate the percentage of voids in the rubber material.

Here, the voids of all sizes that occupy the volume can be evaluated based on $\varphi_{void}$. There is no lower limit of the evaluable size, while the upper limit thereof is the volume irradiated with X-rays.

Examples of the beam used to irradiate the rubber material include X-rays and light, with X-rays being preferred.

When X-rays are used as the beam, the transmittance and scattering intensity of the rubber material may be measured by SAXS analysis. The scattering angle for the SAXS analysis is usually not more than 10 degrees.

The SAXS analysis is usually performed in a region of q represented by the following equation:

$$q = \frac{4\pi \sin(\theta/2)}{\lambda}$$

wherein

θ: scattering angle; and

λ: wavelength of X-rays or neutrons.

The region of q preferably includes $0.001\ \text{Å}^{-1} < q < 0.05\ \text{Å}^{-1}$.

The X-rays scattered in the SAXS analysis may be detected by an X-ray detector 10, and the X-ray detection data from the X-ray detector may be used to generate an image using an image processor or the like, as shown in the FIGURE.

Examples of the X-ray detector 10 include two-dimensional detectors such as X-ray films, nuclear emulsion plates, X-ray image pickup tubes, X-ray fluorescent amplifiers, X-ray image intensifiers, X-ray imaging plates, X-ray CCDs, and X-ray amorphous materials; and line sensor one-dimensional detectors. The X-ray detector may be selected appropriately depending on the type or conditions of the polymer or rubber material 1 to be analyzed, or other factors.

The image processor may appropriately be a common one that can generate X-ray scattering images based on the X-ray detection data from the X-ray detector.

The strain to be applied to the rubber material is preferably an elongational strain, more preferably a uniaxial elongational strain. For example, a uniaxial elongational strain may be applied, for example, by holding the rubber material between a pair of opposing jigs and then elongating the rubber material with the jigs in the respective opposing directions, or by holding the rubber material between a pair of opposing jigs and then elongating the rubber material with one of the jigs, with the other jig being fixed.

The elongation rate at which the elongational strain is applied to the rubber material is usually 100 mm/min to 500 mm/min.

Although the rubber material may have any shape, it preferably has a plate shape or a dumbbell shape as set forth in JIS K 6251 because such a shape facilitates the application of a uniform elongational strain.

The thickness of the rubber material with no strain applied thereto is usually 1 mm to 2 mm.

Examples of rubber components that may be contained in the rubber material include diene rubbers such as isoprene-based rubbers, styrene-butadiene rubbers (SBR), polybutadiene rubbers (BR), acrylonitrile-butadiene rubbers (NBR), chloroprene rubbers (CR), butyl rubbers (IIR), and styrene-isoprene-butadiene copolymer rubbers (SIBR). Each of these rubbers may be used alone, or two or more of these may be used in combination.

The rubber material may contain a filler. Examples of the filler include silica, carbon black, calcium carbonate, talc, alumina, clay, aluminum hydroxide, aluminum oxide, and mica. Preferred among these is silica or carbon black.

The rubber material may contain additives such as stearic acid, zinc oxide, sulfur, and vulcanization accelerators, in addition to the rubber components and fillers.

The rubber material can be prepared by a usual method. Specifically, for example, the rubber material may be prepared by kneading the compounding materials using a kneading machine such as a Banbury mixer or an open roll mill, and then vulcanizing the kneaded mixture.

EXAMPLES

The present disclosure will be specifically described with reference to examples. The examples are not intended to limit the scope of the present disclosure.

<Formulation of Rubber Material>

Styrene-butadiene rubber (HPR850 available from JSR Corporation): 100 parts

Silica (VN3 available from Evonik Degussa): 53 parts

Silane coupling agent: Si266 (bis(3-triethoxysilyl-propyl) disulfide) available from Evonik Degussa): 4.26 parts Sulfur (powdered sulfur available from Tsurumi Chemical Industry Co., Ltd.): 1.5 parts Vulcanization accelerator 1 (NOCCELER NS (N-tert-butyl-2-benzothiazylsulfenamide) available from Ouchi Shinko Chemical Industrial Co., Ltd.): 2.0 parts Vulcanization accelerator 2 (NOCCELER D (1,3-diphenylguanidine) available from Ouchi Shinko Chemical Industrial Co., Ltd.): 2.3 parts <Method of Preparing Rubber Material>

Following the formulation recipe, the compounding components other than the sulfur and vulcanization accelerators were kneaded in a 1.77 L internal Banbury mixer for 3 to 5 minutes until the temperature reached 150° C., to obtain a base-kneaded rubber compound. Next, the base-kneaded rubber compound was kneaded with the sulfur and vulcanization accelerators in an open roll mill, and the resulting kneaded mixture was vulcanized to obtain a rubber material.

The rubber material was sliced into a thickness of 1 mm and then punched into a dumbbell shape as set forth in JIS K 6251 to prepare a specimen, which was used in the following measurements.

Example (SAXS Analysis)

The experiments were conducted at BL20XU of SPring-8. Ion chambers were disposed in front of and behind the specimen, and the specimen was irradiated with X-rays for an exposure time of one second at two-second intervals to determine the scattering intensity and transmittance.

Separately, the same procedure was followed while applying a uniaxial elongational strain to the specimen, to determine the scattering intensity and transmittance. The elongation rate of the specimen was 50 mm/min. The following describes the other conditions.

Brilliance of X-rays (8 keV): $9.5\times10^{15}$ photons/s/mrad$^2$/mm$^2$/0.1% bw Number of photons of X-rays: $10^9$ to $10^{10}$ photons/s Distance from specimen to detector: 2.58 m Detector: PILATUS 100K (Dectris AG)

(Data Processing)

Equation (1) was used to calculate the $\varphi_{void}$. Table 1 shows the results.

Here, the $t_s$ was calculated from the amount (%) of strain using Equation (3).

TABLE 1

| Amount (%) of strain | ∅ void |
|---|---|
| 0 | 0 |
| 100 | 0.019 |
| 150 | 0.053 |
| 200 | 0.065 |

Table 1 shows that in the example the $\varphi_{void}$ increases as the amount of strain increases. Thus, it was demonstrated that the quantitative evaluation of voids can be achieved by comparing the values of $\varphi_{void}$.

Comparative Example

The noise and background were subtracted from the scattering intensity measured in the example, and the (ovoid was calculated using equations (1) to (3) of Non-Patent Literature 2. The change in specimen thickness due to the elongation was corrected using the thickness obtained from the transmittance.

In the comparative example, since the observable wavenumber region was narrow, no quantitative data within the unobserved region was obtained.

Exemplary embodiments of the present disclosure include:

Embodiment 1. An evaluation method, including evaluating a percentage of voids in a rubber material with a strain applied thereto based on a $\varphi_{void}$ calculated from the following Equation (1) using a transmittance and thickness of the rubber material with no strain applied thereto and a transmittance and thickness of the rubber material with the strain applied thereto, $$\phi_{void} = 1 - \rho_s/\rho_0 = 1 - \ln\left(\frac{I_s}{I_0}\right) \Big/ \ln\left(\frac{I}{I_0}\right) \times (t_0/t_s) \tag{1}$$

wherein $\rho_0$: a density of the rubber material with no strain applied thereto, $\rho_s$: a density of the rubber material with the strain applied thereto, $I/I_0$: the transmittance of the rubber material with no strain applied thereto, $I_s/I_0$: the transmittance of the rubber material with the strain applied thereto, $I_0$: an intensity of a beam incident on the rubber material, I: an intensity of the beam transmitted through the rubber material with no strain applied thereto, $I_s$: an intensity of the beam transmitted through the rubber material with the strain applied thereto, $t_0$: the thickness of the rubber material with no strain applied thereto, and $t_s$: the thickness of the rubber material with the strain applied thereto.

Embodiment 2. The evaluation method according to Embodiment 1, wherein the thickness of the rubber material with the strain applied thereto is calculated assuming that the rubber material deforms at a Poisson's ratio of 0.5.

Embodiment 3. The evaluation method according to Embodiment 1 or 2, wherein the strain is an elongational strain.

Embodiment 4. The evaluation method according to Embodiment 3, wherein the elongational strain is a uniaxial elongational strain.

Embodiment 5. The evaluation method according to Embodiment 3 or 4, wherein an elongation rate at which the elongational strain is applied is 100 mm/min to 500 mm/min.

Embodiment 6. The evaluation method according to any combination with any one of Embodiments 1 to 5, wherein the beam is X-rays.

Embodiment 7. The evaluation method according to Embodiment 6, wherein the transmittance and scattering intensity of the rubber material are measured by small-angle X-ray scattering analysis.

Embodiment 8. The evaluation method according to Embodiment 7, wherein the small-angle X-ray scattering analysis is performed in a region of q represented by the following equation:

$$q = \frac{4\pi \sin(\theta/2)}{\lambda}$$

wherein

θ: scattering angle; and

λ: wavelength of X-rays or neutrons.

Embodiment 9. The evaluation method according to Embodiment 8, wherein the region of q includes 0.001 $Å^{-1}$<q<0.05 $Å^{-1}$.

Embodiment 10. The evaluation method according to any combination with any one of Embodiments 1 to 9, wherein the rubber material contains a filler.

Embodiment 11. The evaluation method according to Embodiment 10, wherein the filler is at least one selected from the group consisting of silica, carbon black, calcium carbonate, talc, alumina, clay, aluminum hydroxide, aluminum oxide, and mica.

Embodiment 12. The evaluation method according to any combination with any one of Embodiments 1 to 11, wherein the rubber material contains at least one rubber component selected from the group consisting of isoprene-based rubbers, styrene-butadiene rubbers, polybutadiene rubbers, acrylonitrile-butadiene rubbers, chloroprene rubbers, butyl rubbers, and styrene-isoprene-butadiene copolymer rubbers.

Embodiment 13. The evaluation method according to any combination with any one of Embodiments 1 to 12, wherein the rubber material has a plate shape or a dumbbell shape as set forth in JIS K 6251.

Embodiment 14. The evaluation method according to any combination with any one of Embodiments 1 to 13, wherein a thickness of the rubber material with no strain applied thereto is 1 mm to 2 mm.

The invention claimed is:

1. A method of improving quantitative evaluation of voids in small-angle X-ray scattering analysis of a rubber material, the method comprising:

measuring a transmittance and a thickness of a rubber material with no strain applied thereto and a transmittance and a thickness of the rubber material with the strain applied thereto based on X-ray detection data detected from an X-ray detector; and evaluating a percentage of voids in the rubber material with the strain applied thereto based on a $\varphi_{void}$ calculated from the following Equation (1) using the transmittance and the thickness of the rubber material with no strain applied thereto and the transmittance and the thickness of the rubber material with the strain applied thereto:

$$\phi_{void} = 1 - p_s/p_0 = 1 - \text{In}\left(\frac{I_s}{I_0}\right)/\text{In}\left(\frac{I}{I_0}\right) \times (t_0/t_s) \tag{1}$$

where $\rho_0$: a density of the rubber material with no strain applied thereto, $\rho_s$: a density of the rubber material with the strain applied thereto, $I/I_0$: the transmittance of the rubber material with no strain applied thereto, $I_s/I_0$: the transmittance of the rubber material with the strain applied thereto, $I_0$: an intensity of an X-ray beam incident on the rubber material, I: an intensity of the X-ray beam transmitted through the rubber material with no strain applied thereto, $I_s$: an intensity of the X-ray beam transmitted through the rubber material with the strain applied thereto, $t_0$: the thickness of the rubber material with no strain applied thereto, and $t_s$: the thickness of the rubber material with the strain applied thereto, wherein the evaluation step comprises determining the percentage of voids in a region inside and a region outside an observable wavenumber region of the X-ray detector to quantitatively evaluate the voids in the rubber material.

2. The evaluation method according to claim 1, wherein the thickness of the rubber material with the strain applied thereto is calculated based on an assumption that the rubber material deforms at a Poisson's ratio of 0.5.

3. The evaluation method according to claim 1, wherein the strain is an elongational strain.

4. The evaluation method according to claim 1, wherein the rubber material comprises a filler.

5. The evaluation method according to claim 1, wherein the evaluation step comprises determining the percentage of voids in the region inside and the region outside the observable wavenumber region of the X-ray detector to quantitatively evaluate the voids in an entire rubber material.

6. The evaluation method according to claim 1, wherein the measurement step comprises measuring the transmittance and the thickness of an entire rubber material with no strain applied thereto and the transmittance and the thickness of the entire rubber material with the strain applied thereto based on the X-ray detection data detected from the X-ray detector.

7. The evaluation method according to claim 1, wherein the strain is an elongational strain, and an elongation rate at which the elongational strain is applied is in a range of 50 mm/min to 500 mm/min.

8. The evaluation method according to claim 1, wherein the X-ray detector is configured to measure the transmittance and the thickness of the rubber material by irradiating with X-rays for an exposure time of one second at two-second intervals to determine the transmittance and the thickness.

9. A method of improving quantitative evaluation of voids in small-angle X-ray scattering analysis of a rubber material, the method comprising:

measuring a transmittance and a thickness of an entire rubber material with no strain applied thereto and a transmittance and a thickness of the entire rubber material with the strain applied thereto based on X-ray detection data detected from an X-ray detector; and evaluating a percentage of voids in the entire rubber material with the strain applied thereto based on a $\varphi_{void}$ calculated from the following Equation (1) using the transmittance and the thickness of at least a portion of the entire rubber material with no strain applied thereto and the transmittance and the thickness of the portion of the rubber material with the strain applied thereto:

$$\phi_{void} = 1 - p_s/p_0 = 1 - \text{In}\left(\frac{I_s}{I_0}\right)/\text{In}\left(\frac{1}{0}\right) \times (t_0/t_s) \tag{1}$$

where $\rho_0$: a density of the portion of the rubber material with no strain applied thereto, $\rho_s$: a density of the portion of the rubber material with the strain applied thereto, $I/I_0$: the transmittance of the portion of the rubber material with no strain applied thereto, $I_s/I_0$: the transmittance of the portion of the rubber material with the strain applied thereto, $I_0$: an intensity of an X-ray beam incident on the portion of the rubber material, I: an intensity of the X-ray beam transmitted through the portion of the rubber material with no strain applied thereto, $I_s$: an intensity of the X-ray beam transmitted through the portion of the rubber material with the strain applied thereto, $t_0$: the thickness of the portion of the rubber material with no strain applied thereto, and $t_s$: the thickness of the portion of the rubber material with the strain applied thereto, wherein the evaluation step comprises determining the percentage of voids in a region inside and a region outside an observable wavenumber region of the X-ray detector to quantitatively evaluate the voids in the entire rubber material.

10. The method of improving quantitative evaluation of voids according to claim 9, wherein the strain is an elongational strain, and an elongation rate at which the elongational strain is applied is in a range of 50 mm/min to 500 mm/min.

11. The method of improving quantitative evaluation of voids according to claim 9, wherein the X-ray detector is configured to measure the transmittance and the thickness of the rubber material by irradiating with X-rays for an exposure time of one second at two-second intervals to determine the transmittance and the thickness.

* * * * *